United States Patent [19]

Brownell et al.

[11] 4,370,240

[45] Jan. 25, 1983

[54] REMOVAL OF IRON COMPOUNDS FROM ORGANIC PROCESS STREAMS

[75] Inventors: George L. Brownell, Mt. Lebanon Township, Allegheny County; William R. Davie, Hopewell Township, Beaver County; Marvin C. Fields, Wilkins Township, Allegheny County, all of Pa.

[73] Assignee: United States Steel Corporation, Pittsburgh, Pa.

[21] Appl. No.: 272,141

[22] Filed: Jun. 10, 1981

[51] Int. Cl.$^3$ ............................................. B01D 15/04
[52] U.S. Cl. ..................................................... 210/673
[58] Field of Search ............... 210/660, 673, 678, 684, 210/685, 688; 568/749, 758

[56] References Cited

U.S. PATENT DOCUMENTS

| | | | |
|---|---|---|---|
| 3,395,099 | 7/1968 | Johnson | 210/678 |
| 3,425,937 | 2/1969 | Weiss et al. | 210/673 |
| 3,715,339 | 2/1973 | Rainer | 210/688 |
| 4,107,218 | 8/1978 | Konrad et al. | 260/724 |
| 4,115,260 | 9/1978 | Avery | 210/684 |
| 4,157,298 | 6/1979 | van den Berg et al. | 210/684 |
| 4,327,229 | 4/1982 | Mendiratta | 568/758 |

*Primary Examiner*—Ivars C. Cintins
*Attorney, Agent, or Firm*—William L. Krayer

[57] ABSTRACT

Weakly basic ion exchange resins are used to remove iron compounds in anhydrous or substantially anhydrous organic systems such as phenolic process streams. The resins may be either in the form of a weak salt such as the amine hydrochloride or may be a protonated amine carboxylic acid in the acidic form. In either case, we have determined that the active site does not perform in a conventional ion exchange manner but rather forms a complex with the entire iron compound molecule. While the complex is formed in a waterless or almost waterless system, it may be regenerated in an aqueous system.

7 Claims, No Drawings

REMOVAL OF IRON COMPOUNDS FROM ORGANIC PROCESS STREAMS

BACKGROUND OF THE INVENTION

Iron compounds are and can be extremely detrimental to certain organic process streams such as phenolic process streams utilized in the manufacture of bisphenol-A (BPA), which has very low tolerances for iron when the product is to be used for making polycarbonates.

Detrimental levels of iron may find their way into such process streams in processes which employ acid and in which are present ferrous metal parts, pipes, vessels or the like. In spite of strenuous and careful efforts to prevent corrosion, iron contaminants may enter the process far upstream from the final product and still present problems of meeting specifications for the final product.

Specifically with respect to the treatment of bisphenol-A to purify it, the reader may be interested in U.S. Pat. No. 4,107,218, which describes a process of removing color bodies from bisphenol-A wherein the bisphenol-A is passed through a bed of cation exchange resin (a resin which exchanges cations) such as a conventional styrene-divinyl benzene resin wherein a certain portion of the styrene is sulfonated to place strongly anionic sites on the resin. There is much discussion in the patent's specification about the regeneration of the resin in a phenol/water mixture, which then for economic reasons has to be reclaimed by distillation.

Also of interest is East German Pat. No. 134,427, which suggests the use of acid ion exchange resin for the purification of phenol; specifically, various organic impurities are removed by passing the phenol through a bed of acidic ion exchange resin (that is, one containing fixed acid sites capable of exchanging cations).

U.K. Pat. No. 1,539,186 suggests the use of sulfonated styrene/divinylbenzene ion exchange resins which have been partly neutralized with aminothiol-carboxylic acids or esters as catalysts for the manufacture of bisphenol-A from acetone and phenol in a water-dry system.

German Offenlegungschrift No. 2,048,661 discloses the use of fixed beds of strongly acidic and weakly basic ion exchange resins to purify raw bisphenol-A; however, the chemical structure of the resin is not given, nor is a description of the impurities removed. The specification states: "The mechanism of the purification step in the exchange column is not known. It is surmised that in the purification step such components are removed as affect the decomposition of the raw bisphenol-A during distillation, such as acids, alkalies, salts, traces of heavy metals, etc." After treatment with the resin, the product is subjected to a vacuum distillation step to separate the phenol from the bisphenol-A. No description of regeneration is given.

None of the above references addresses the problem of the elimination of iron compounds from the bisphenol-A (BPA) product which are obtained when the BPA is made using a hydrochloric acid catalyst for the reaction of phenol and acetone in contact with even a small surface containing ferrous metal. Also, it is known that conventional ion exchange resins such as the sulfonic acid (strong acid) or carboxylic acid (weak acid) types can be used to remove iron from phenol systems containing more than about 5% water but they will not remove ferric chloride from almost anhydrous phenolic streams. Apparently these conventional ion exchange resins depend upon ionization of the iron salts for their removal but insufficient ionization takes place in phenolic systems containing less than 5% water.

SUMMARY OF THE INVENTION

We have found a novel process for efficient removal of ferric chloride from anhydrous or nearly anhydrous phenolic solutions using a special class of ion exchange resins in a specific ionic form. These resins form a complex with ferric chloride that does not require water for ionization of the iron salt. In fact, ionization of the iron salt by water inhibits the complexing action of the resins and their effectiveness is greatly diminished as the water content of the system increases above 5%. The resins do not operate in an ion exchange mode in this invention. The anhydrous or nearly anhydrous phenolic compositions which we treat to remove iron comprise phenol of at least 90% purity, the other 10% being water and other organics, or, more typically, phenol containing material amounts only of water (normally up to 5% or at the very most 10%) and (up to 2 or 3%) bisphenol-A.

The active form of the resin may be represented by the group $R_3NH^+$ which forms a complex with ferric chloride represented as $R_3NH \cdot FeCl_3^+$. This complex is stable and the ferric chloride is removed from the solution so long as the system is anhydrous or almost anhydrous. This system is also quite novel in that the iron can be released from the resin and the resin completely regenerated or almost completely regenerated by merely washing with water. The water ionizes and hydrates the system to split the complex into $R_3NH^+$ (regenerated form of the resin) and $FeCl_3$ which washes off the resin in a hydrated form.

The ion exchange resins that function in this manner are weakly basic resins in the form of a salt with a strong or a weak acid. The nature of the "backbone" of the resin is not critical but generally it is a styrene-divinylbenzene copolymer. The required reactive side groups, or reactive sites, on this copolymer are amines in their salt forms which may be the radical $—NR_2H^+$ where R may be alkyl, alkaryl, or aryl. A common class of resins that fit this description contains the group

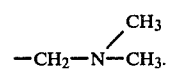

These weakly basic ion exchange resins ordinarily are almost exclusively used in the free base form to remove acids from process streams. Resins of this type in the form of an acid salt are the subject of this invention.

One of the preferred systems is the hydrochloride salt of a weakly basic ion exchange resin—represented by the radical $—CH_2N(CH_3)_2H^+Cl^-$. This group in a nearly anhydrous medium forms a complex with ferric chloride which may be represented as $—CH_2N(CH_3)_2H^+FeCl_4^-$ and the iron is removed from the solution. When water is added to this complex, ferric chloride is washed off and the resin is converted back to its hydrochloride salt form which when put back into a nearly anhydrous system will again remove ferric chloride from solution.

There are a number of commercially available weakly basic ion exchange resins. All of these weakly basic ion exchange resins in their salt forms are effective for ferric chloride removal in anhydrous phenolic systems. However, for maximum resin capacity, resin stability, ease of regeneration and a minimum of possible side reactions, we prefer resins such as the Rohm & Haas Amberlites IRA-93 or IRA-94. These are macroreticular, weakly basic resins with tertiary amine functionality on a styrene divinylbenzene "backbone" in bead form. The macroreticular structure is a discrete porous network that permits more complete adsorption and desorption of large molecules. They are especially resistant to attrition, chemical attack, and osmotic shock.

Another of the preferred resin systems contains both the weakly basic tertiary amine group and the acidic group in the same radical. These resins can form internal salts and are referred to as chelating resins. Their "backbone" and the attached radicals are very similar to the system previously discussed and can be represented by the radical

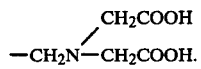

In their acidic form they may be expressed

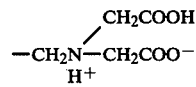

and in anhydrous systems form the ferric chloride complex analagous to the one formed by the hydrochloride form of the weak base resin

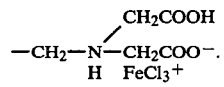

This chelating resin—ferric chloride complex also is decomposed by a water wash and the resin is "regenerated" but the second carboxyl (COOH) group in aqueous systems behaves like a weak acid ion exchange resin and complexes with the ionized ferric ion. The water regenerated resin therefore will still contain this residual iron which has essentially no detrimental effect on ferric chloride removal from anhydrous phenolic systems.

For regeneration with complete iron removal from this resin a conventional acid washing technique is required after the water wash.

The "chelating" resin has the advantage of behaving like a conventional weak acid ion exchange resin in systems with more than 5% water present so it also may remove iron if the composition of the stream to be treated occasionally fluctuates to higher water content. In that mode of operation, however, its iron capacity is not high.

Either type of resin system—salt of weak base resin or chelating resin in the acid form—may be used. The resin choice depends on the stream being treated. The "chelating" resin is the more expensive and has a lower initial iron capacity. It can have capacity for ionic iron in systems with more than 5% water if it has previously been completely regenerated by an acid wash. Acid wash and complete iron removal are not necessary if the resin is used in essentially anhydrous media. This protective iron removal capability in systems which occasionally fluctuate above 5% water could be accomplished by a separate conventional strong acid ion exchange resin column following the column of salt of weak base resin. (Amberlite IRA-93 hydrochloride followed by Amberlite IRC-200H, for example).

The chelating ion exchange resins are available commercially from Dow and from Rohm & Haas. The Rohn & Haas resin Amberlite IRC-718 is a cross-linked macroreticular cation exchange resin with selectivity for transition metal cations over alkali or alkaline earth cations. Its highly cross-linked structure makes it highly resistant to physical breakdown due to osmotic shock. These chelating resins are generally used almost exclusively in their sodium form for removal of transition metal ions from aqueous systems and commercially have been available only in the sodium form. The sodium form is not operable in non-aqueous systems because it depends on ionization for ion removal to occur—additionally if it did remove iron, it would release sodium into the system and this also would be objectionable in the BPA streams since basic ions can catalyze BPA decomposition. In our tests, the free base form of the weak base ion exchange resin Amberlite IRA-93, surprisingly, had a high capacity for ferric chloride removal but even from the very start of the run, unacceptably high levels of iron leaked through the resin bed.

While the acidic (hydrochloride) form of the weak base resin IRA-93 is regenerated essentially completely with water (negligible residual iron on the resin), after several cycles the iron adsorption capacity of the resin decreases. Presumably this is due to slight hydrogen chloride loss from the resin during the loading and/or water regeneration cycles. The resin capacity for ferric chloride can be restored with occasional addition of hydrogen chloride at the end of regeneration cycles.

As can be seen from the Tables, the iron removal efficiency of these resin systems falls off so rapidly above 5% water concentration in the phenol that they become impractical and above 10% water concentration they are very poor.

These resins should not be seriously considered for use if water content of the phenolic streams is continuously above 10%. At this water level, conventional strong acid resins are satisfactory. If the water content of the phenolic stream is continuously above 5% but only occasionally above 10%, the chelating form of resin is to be preferred and it should be completely regenerated with acid wash after water wash in each cycle. The acidic form of the weak base resin, because of its much higher capacity, and regeneration only with water wash, may be the preferred resin for use if the water content of the system is seldom above 5%.

While one might postulate that the acetone form of IRA-93 would be as effective for iron removal as the chelating resin, Amberlite IRC-718, since it is essentially the same ionic species, it apparently dissociates and the acetic acid washes off slowly yielding the free base form in a manner similar to the acidic (hydrochloride) form. The chelating resin, by contrast, cannot lose its salt forming weak acid since it is part of the same molecule.

It is important to stress that the resins do not act in an ion exchange mode in the process of removing iron from the anhydrous or almost anhydrous systems. The resins form a complex that is stable under essentially anhydrous conditions and this complex is dissociated by water.

Table A shows the results of laboratory tests which are more or less self-explanatory.

TABLE A

| Resin | Resin Form | Wt. of Wet Resin | Depth of Resin Bed | Water Content of Feed | Cumulative Feed Volume | Effluent Iron | |
|---|---|---|---|---|---|---|---|
| 1000 ppm Fe as FeCl₃ in feed | | | | Resin Bed Volumes About 250 cc | | | |
| Column Jacket Temperature 65° C. | | | | Feed Rate 30 cc/min. | | | |
| Amberlite IRA-93 | hydrochloride | 115 grams | 23 inches | 0% | 4 quarts | 0.1 | ppm |
| | | | | | 8 " | 0.45 | |
| | | | | | 9 " | 0.45 | |
| | | | | | 10 " | 7.35* | |
| Same column after first water regeneration | | | | | 4 quarts | 0.1 | ppm |
| | | | | | 8 " | 0.8 | ppm |
| | | | | | 9 " | 1.7* | |
| Same column after second water regeneration | | | | | 4 quarts | <0.1 | |
| | | | | | 7 " | 0.4 | |
| | | | | | 8 " | 9.8* | |
| Same column after the next regeneration & HCl wash | | | | | 4 quarts | 0.1 | |
| | | | | | 7 " | 0.5 | |
| | | | | | 8 " | 0.6 | |
| | | | | | 9 " | 27.5* | |
| Same column after regeneration & HCl wash | | | | 5% | 4 quarts | 0.16 | |
| | | | | | 7 " | 5.8* | |
| | | | | | 8 " | 42 | |
| Same column after regeneration & HCl wash | | | | 10% | 4 quarts | 30* | |
| | | | | | 6 " | 63 | |
| Same column after regeneration & HCl wash | | | | 20% | 1 quart | 64* | |
| Amberlite IRA-93 | free base | 115 grams | 23 inches | 0% | 1 quart | 2.7* | |
| | | | | | 2 quarts | 8.8 | |
| | | | | | 4 " | 13.5 | |
| | | | | | 6 " | 23 | |
| | | | | | 7 " | 44 | |
| Amberlite IRA-93 | acetate | 115 grams | 23 inches | 0% | 1 quart | 4* | |
| | | | | | 2 quarts | 11.5 | |
| | | | | | 4 " | 94 | |
| | | | | | 5 " | 111 | |
| | | | | | 10 " | 129 | |
| Amberlite IRC-718 | acid | 140 grams | 20 inches | 0% | 1 quart | 0.17 | |
| | | | | | 2 quarts | 0.18 | |
| | | | | | 3 " | 0.23 | |
| | | | | | 4 " | 0.28 | |
| | | | | | 5 " | 7.8* | |
| Same column after first water regeneration | | | | | 1 quart | 0.14 | |
| | | | | | 2 quarts | 0.24 | |
| | | | | | 3 " | 1.15 | |
| | | | | | 4 " | 3.95* | |
| Same column after second water regeneration | | | | | 1 quart | 0.1 | |
| | | | | | 2 quarts | 0.7 | |
| | | | | | 3 " | 32* | |
| Same column after water and HCl regeneration | | | | | 4 quarts | 1.3 | |
| | | | | | 5 " | 29.3* | |
| Amberlite IRC-718 | acid | fresh resin | | 5% | 2 quarts | 0.2 | |
| | | | | | 3 " | 0.5 | |
| | | | | | 4 " | 10* | |
| Fresh resin again | | | | 10% | 1 quart | 0.1 | |
| | | | | | 2 quarts | 0.4 | |
| | | | | | 3 " | 9.1* | |
| Fresh resin again | | | | 20% | 1 quart | 0.4 | |
| | | | | | 2 quarts | 62* | |
| Amberlite IRC-718 | sodium | 180 grams | 19¼ in. | 0% | 1 quart | 1.1* | |
| | | | | | 2 quarts | 3.8 | |
| | | | | | 3 " | 9.2 | |

*Above 1 ppm iron considered to be breakthrough

Resin capacity for FeCl₃ was determined for feed concentrations of FeCl₃ from 10 to 100 ppm solutions and for water concentrations from 0.3 to 3 percent (Table B). As expected from the mechanism of action of Amberlite IRC-718, increasing the water content of the feed to the column even to only 3 percent (Test 3) tended to reduce the exchange rate of the FeCl₃. A water content above 5 percent caused elution of iron and HCl from the resin column (Table C).

The calculated resin capacity is about 0.15 lb $Fe^{+++}/ft^3$ resin in the very small bed and fast flow rate (Test 2). It is about 1 lb $Fe^{+++}/ft^3$ resin in the larger column (Test 1). The lower measured bed capacity (to breakthrough) of Test 2 compared to Test 1 is not believed to be primarily of consequence of the lower iron concentration in the feed (10 ppm versus 100 ppm), but rather to be a consequence of the fact that the wave front of iron concentration would have a much more profound effect in the very short bed of Test 2 compared to its effect in the much longer bed of Test 1. [A very short bed and high flow rate had to be used in Test 2 to obtain an estimate of capacity to breakthrough in reasonable operating time for dilute (10 ppm) iron solutions.]

A water content of greater than 5 percent in the phenol will elute some of the iron from an iron-loaded IRC-718 resin (Table C), an effect which is detrimental to the system. If the iron-saturated resin is washed with water, about 50 percent of the iron is removed as FeCl₃, and the remaining chloride associated with the iron is eluted as HCl. There may be two reasons for the release of the iron during water washing. First, the functional groups operate in a different manner in aqueous (ionized) than in non-aqueous (non-ionized) systems, and therefore the capacity of the resin could change drastically in going from aqueous to non-aqueous. Second, as ionized $FeCl_3$ reacts with the carboxyl groups of the resin, HCl is released, and since HCl is used to regenerate (remove iron) this resin, this localized high concentration of HCl may serve to remove iron from the resin. This iron removal from the resin with water was capitalized on in regeneration studies, which are described in a subsequent section.

If the water content of the phenol stream becomes too high, because of special variations in the process, iron is not removed by IRC-718, and, as indicated earlier, it may be released from the resin. The $FeCl_3$ will be ionized, and thus a strong acid type resin will be helpful to remove the $Fe^{+++}$ ion and prevent it from entering the reactors. Additionally, ferrous iron will be removed by the strong acid type resin.

Because the strong acid resin Amberlite 200C(H) is so much more dense than IRC-718, it is charged to the bottom of the column to make a stratified bed.

A stratified resin bed and a resin bed of only Amberlite IRC-718(H) were prepared and evaluated. Phenol solution pumped from commercial reactors at shutdown was used for the test. This solution contained 3.5% water, 2.12% BPA, 7.7 ppm iron, and 26.9 ppm chlorides. The results of that test indicate that the stratified resin bed was better than the IRC-718 bed alone. About 615 bed volumes of the 7.7 ppm iron solution were processed through the stratified bed without a breakthrough (<1 ppm iron); whereas, with the IRC-718 resin alone, breakthrough occurred after about 446 bed volumes had been processed through the resin. Although these results show that the IRC-718 resin alone is less effective than the stratified IRC-718/200C(H) bed, they also show that IRC-718 is very effective for removal of iron from a plant phenol stream. The relatively high water content of the test solution (3.5%) probably accounted for these results because it increased the effectiveness of the 200C(H) resin and decreased the effectiveness of the IRC-718 resin.

Backwashing with 90% phenol was successful in correcting clogging; resetting was not a problem, as the strong acid resin went directly to the bottom of the vessel. Data from this test are presented in Table D.

IRC-718 resin effectively removes ferric iron from phenolic solutions containing less than 3 percent water. However, as previously shown, its effectiveness decreases with increasing water content.

Ferrous iron is not readily removed from phenol by IRC-718. The hydrogen form of IRC-718 has no tendency to remove $Fe^{++}$ from aqueous solutions because of an unfavorable selectivity constant. However, it is possible that in anhydrous or nearly anhydrous systems, the ferrous iron may be removed as ferrous chloride ($FeCl_2$). Because of the very low solubility of $FeCl_2$ in phenol (about 20 ppm or less) and the tendency for $Fe^{++}$ to readily oxidize to $Fe^{+++}$, it has not been possible to determine unequivocally whether IRC-718(H) removes ferrous iron from phenol that contains very small amounts of water.

The large losses of iron and chloride observed previously when washing the loaded IRC-718 resin with water suggested that the resin could be at least partially regenerated simply by water-washing. To test this idea, a 15-inch-deep column was loaded (to breakthrough) with phenol containing 1000 ppm iron to measure the resin capacity. The column was then water-washed. Then, phenol containing 10 ppm iron was passed through the resin to test if the water-regenerated resin could reduce "normal" iron loadings to very low values. The resin was then loaded (with 1000 ppm iron feed) to test the capacity of the water-regenerated resin. The procedure was then repeated. The results were:

Measured capacity for initial loading = 1.6 lb iron/ft$^3$ resin

Iron in effluent phenol (10 ppm iron in feed) after first water wash = <0.01 ppm Measured capacity after first water wash = 1.2 lb iron/ft$^3$ resin Iron in effluent phenol (10 ppm iron in feed) after second water wash = <0.01 ppm Measured capacity after second water wash = 0.8 lb iron/ft$^3$ resin Thus, after one water wash, the resin exhibited 75 percent of its initial capacity, and after two water washes, the resin exhibited 50 percent of its original capacity.

Two laboratory procedures were used for the water regeneration (the water temperature was 65° C. and the water flow rate was approximately 3 bed volumes per hour in both cases). In the first procedure, the phenol was displaced (downward flow) with water, and water flow was continued to achieve regeneration. A total of three bed volumes of water was used. In the second procedure, the phenol was first drained from the column. Air was then displaced from the column by water upflow. This was followed by downflow of three or four bed volumes of water to regenerate the column. Both procedures were equally effective.

It was found that substituting dilute hydrochloric acid (6.7%) for water in either of the two regeneration procedures described above would result in complete regeneration of the resin. The column could then be rinsed to neutrality with 3 bed volumes of water.

TABLE B

| | | | Amberlite IRC-718 - Iron Capacity | | | | | | |
|---|---|---|---|---|---|---|---|---|---|
| | | | Composition of Feed | | | | | Iron in | Resin |
| Test No. | Feed, gal | Resin Bed Vol, cc | $Fe^{+3}$, ppm | Phenol, % | BPA, % | Water, % | Flow Rate, Bed Vol/hr | Tempera- ture, °C. | Effluent, ppm | Capacity, lb/ft$^3$ |
| 1 | 1 | 200[1] | 100 | 98.7 | 1 | 0.3 | 10 | 60-65 | <0.1 | |
| | 2 | | | | | | | | <0.1 | |
| | 3 | | | | | | | | <0.1 | |
| | 4 | | | | | | | | 0.9[2] | |
| | 5 | | | | | | | | 0.5 | |
| | 6 | | | | | | | | 0.4 | |
| | 7 | | | | | | | | 1.1 | |
| | 8 | | | | | | | | 1.8 | 1.0 |
| 2 | 1 | 37[3] | 10 | 99.0 | 1 | 1.0 | 60 | 60-65 | 0.15 | |

TABLE B-continued

Amberlite IRC-718 - Iron Capacity

| Test No. | Feed, gal | Resin Bed Vol, cc | Fe$^{+3}$, ppm | Phenol, % | BPA, % | Water, % | Flow Rate, Bed Vol/hr | Temperature, °C. | Iron in Effluent, ppm | Resin Capacity, lb/ft$^3$ |
|---|---|---|---|---|---|---|---|---|---|---|
|  | 2 |  |  |  |  |  |  |  | 0.27 |  |
|  | 3 |  |  |  |  |  |  |  | 0.42 |  |
|  | 4 |  |  |  |  |  |  |  | 0.61 |  |
|  | 5 |  |  |  |  |  |  |  | 1.16$^{(2)}$ |  |
|  | 6 |  |  |  |  |  |  |  | 0.58 |  |
|  | 7 |  |  |  |  |  |  |  | 1.4 |  |
|  | 8 |  |  |  |  |  |  |  | 2.0 |  |
| 3 | 1 | 37 | 10 | 97.0 | 1 | 3.0 | 60 | 60-65 | 0.94 | 0.5 |
|  | 2 |  |  |  |  |  |  |  | 1.15 |  |
|  | 3 |  |  |  |  |  |  |  | 1.45 |  |
|  | 4 |  |  |  |  |  |  | 30 | 0.35 |  |
|  | 5 |  |  |  |  |  |  |  | 1.8 |  |
|  | 6 |  |  |  |  |  |  |  | 2.8 |  |
|  | 7 |  |  |  |  |  |  |  | 2.3 |  |
|  | 8 |  |  |  |  |  |  | 15 | 0.9 |  |

$^{(1)}$Bed length - 21 inches.
$^{(2)}$Initial sample after standing overnight.
$^{(3)}$Bed length = 4 inches.

TABLE C

Effect of Water on FeCl$_3$-Saturated Amberlite IRC-718

Load Cycle
Feed
Fe$^{+3}$ - 100 ppm
H$_2$O - 5%
Phenol - 95%
Flow 9 bed volumes/hour
Temperature - 55-60° C.

| Effluent, gal | Effluent Composition | |
|---|---|---|
|  | Cl$^-$, ppm | Fe, ppm |
| 1 | 4.5 | 0.01 |
| 2 | — | 0.01 |
| 3 | 5.0 | 0.5 |
| 4 | — | 0.7 |
| 5 | 7.1 | 1.2 |
| 6 | — | 1.8 |
| 7 | 11.6 | 2.7 |
| 8 | 12.3 | 3.2 |

Water Contact Test*

| Phenol/Water Composition - One Quart Each of: | | |
|---|---|---|
| 95% phenol/5% water | 11.9 | 2.5 |
| 90% phenol/10% water | 143 | 43 |
| 85% phenol/15% water | 711 | 69 |
| 80% phenol/20% water | 1102 | 85 |

*At conclusion of load cycle, the resin was contacted successively with one quart each of a 5, 10, 15, 20% aqueous phenol solution.

TABLE D

Phenol Stream - Stratified Bed

Analysis of feed:
Iron - 7.7 ppm
Chloride - 26.9 ppm
Water - 3.5%
BPA - 2.12%
phenol - balance

| | IRC 718 Resin | | | IRC 718 + 200 CH Mixed Bed | | |
|---|---|---|---|---|---|---|
| Time | Flow Ml/min | Iron ppm | Chloride ppm | Flow Ml/min | Iron ppm | Chloride ppm |
| 0903 | 33 |  |  | 27 |  |  |
| 1100 |  | 0.11 | 8.7 |  |  |  |
| 1200 | 32 |  |  | 38.5 | 0.11 | 25.7 |
| 1300 |  | 0.08 | 19.7 |  | 0.11 | 13.1 |
| 1400 | 27 |  |  | 31 |  |  |
| 1500 |  | 0.11 | 11.8 |  | 0.16 | 27.7 |
| 1600 | 25 |  |  | 32.5 |  |  |
| 1700 |  | 0.07 | 8.6 |  | 0.31 | 18.1 |
| 1800 | 22 |  |  | 31.5 |  |  |
| 1900 |  | 0.17 | 23.9 |  | 0.10 | 13.5 |
| 2000 | 19 |  |  | 30.5 |  |  |
| 2100 |  | 0.03 | 13.9 |  | 0.12 | 19.7 |
| 2200 | 17.5 |  |  | 30.5 |  |  |
| 2300 |  | 0.04 | 10.9 |  | 0.01 | 34.8 |
| Total flow | 19.32 liters | | | 25.98 liters | | |
| 0900 | 6 |  |  | 30 |  |  |
| 1000 |  | 0.32 | 1.1 |  | 0.39 | 12.2 |
| 1130 | 5 |  |  | 28 |  |  |
| 1200 |  |  |  |  | 0.58 | 11.5 |
| 1400 | Backflush with 750 ml 90% phenol | | | | | |
| 1400 | 10 |  |  | 32.5 | 0.59 | 12.4 |
| 1600 | 8 |  |  | 29.5 |  |  |
| 1700 |  | 0.30 | 4.5 |  | 0.26 | 15.3 |
| 1800 | 7.5 |  |  | 30 |  |  |
| 1900 |  | 0.35 | 3.0 |  | 0.24 | 18.1 |
| 2000 | 7 |  |  | 26 |  |  |
| 2100 |  | 0.21 | 3.4 |  | 0.22 | 16.7 |
| 2200 | 7 |  |  | 23.5 |  |  |
| 2300 |  | 0.22 | 2.3 |  | 0.22 | 15.6 |
| Total flow | 25.23 liters | | | 50.43 liters | | |
| 1000 | 5.8 |  |  | 20 |  |  |
| 1100 |  | 0.32 | 3.6 |  | 0.52 | 14.1 |
| 1245 | Backflush |  |  |  |  |  |
| 1300 |  |  |  |  | 0.26 | 13.1 |
| 1400 |  |  |  | 14 |  |  |
| 1600 | 31 |  |  | 14.5 |  |  |
| 1700 |  | 0.20 | 4.0 |  | 0.23 | 11.0 |
| 1800 | 23 |  |  | 11.5 |  |  |
| 1900 |  | 0.17 | 4.1 |  | 0.27 | 11.5 |
| 2000 | 18 |  |  | 7.5 |  |  |
| 2100 |  | 0.22 | 3.8 |  | 0.28 | 10.5 |
| 2200 | 15 |  |  | 5.5 |  |  |
| 2300 |  | 0.21 | 3.0 |  | 0.28 | 10.9 |
| Total flow | 36.40 liters | | | 59.76 liters | | |
| 0900 |  |  |  | 16.5 |  |  |
| 1000 |  | 0.19 | 5.4 |  | 0.42 | 12.7 |
| 1100 | 16 |  |  | 13.5 |  |  |
| 1200 |  | 0.22 | 4.3 |  | 0.15 | 11.5 |
| 1300 | 13 |  |  | 10.5 |  |  |
| 1400 |  | 0.22 |  |  | 0.21 |  |
| 1500 | 10 |  |  | 10 |  |  |
| 1600 |  | 0.20 | 4.0 |  | 0.41 | 13.8 |
| Total flow | 41.26 liters | | | 69.45 liters | | |
| 0800 | 13.5 |  |  | 10 |  |  |

TABLE D-continued
Phenol Stream - Stratified Bed

Analysis of feed:
- Iron - 7.7 ppm
- Chloride - 26.9 ppm
- Water - 3.5%
- BPA - 2.12%
- phenol - balance

| | IRC 718 Resin | | | IRC 718 + 200 CH Mixed Bed | | |
|---|---|---|---|---|---|---|
| Time | Flow Ml/min | Iron ppm | Chloride ppm | Flow Ml/min | Iron ppm | Chloride ppm |
| 0900 | | 0.30 | 14.1 | | 0.70 | 4.5 |
| 1000 | 13 | | | 10 | | |
| 1100 | | 0.60 | 10.6 | | 0.40 | 3.4 |
| 1200 | 13.5 | | | 8.0 | | |
| 1300 | | 0.50 | 11.1 | | 0.40 | 4.8 |
| 1400 | 13 | | | 4.5 | | |
| 1500 | | 0.50 | 4.9 | Backflushed - lost approx. 20% of the resin. | | |
| Total flow | 46.72 liters | | | 68.79 liters | | |
| 0800 | | 1.4 | 7.1 | | 3.6 | 12.5 |
| 0900 | 13 | | | 31 | | |
| 1000 | | 1.5 | 5.6 | | 1.0 | 5.5 |
| 1100 | 12 | | | 32 | | |
| 1200 | | 1.4 | 5.8 | | 1.6 | 11.6 |
| 1300 | 11.5 | | | 16 | | |
| 1400 | | 1.4 | 3.5 | | 0.40 | 12.1 |
| 1500 | 10.5 | | | 16 | | |
| Total flow | 51.04 liters | | | 78.29 liters | | |
| 0800 | 10 | | | 15 | | |
| 0900 | | 0.38 | 16.6 | | 0.78 | 1.7 |
| 1000 | 11.5 | | | 16.5 | | |
| 1100 | | 0.54 | 14.8 | | 0.49 | 5.4 |
| 1200 | 11 | | | 16 | | |
| 1300 | | 0.60 | 15.4 | | 0.49 | 0 |
| 1400 | 11.5 | | | 17 | | |
| 1500 | | 0.40 | 16.1 | | 0.44 | 4.7 |
| Total flow | 55.66 liters | | | 85.01 liters | | |
| 0900 | 10 | 0.21 | 12.6 | 14 | 0.34 | 9.3 |
| 1000 | 10 | | | 15 | | |
| 1100 | | 0.19 | 14.8 | | 0.24 | 22.5 |
| 1200 | 9.5 | | | 16 | | |
| 1300 | | 0.83 | 23.7 | | 0.24 | 5.1 |
| 1400 | 9 | | | 16 | | |
| 1500 | | 0.16 | 16.4 | | 0.20 | 4.8 |
| Total flow | 59.08 liters | | | 90.41 liters | | |
| 0800 | 9 | 0.28 | 5.7 | 15 | 0.26 | 13 |
| 1000 | 6 | 0.20 | 5.1 | 14 | 0.27 | 15.5 |
| 1200 | | | | 15 | 0.25 | 17.9 |
| | Backflush | | | | | |
| Total Flow | 59.98 liters | | | 94.01 liters | | |
| 0800 | 15 | | | 18 | | |
| 0900 | | 0.18 | 7.2 | | 0.24 | 4.0 |
| 1000 | 10 | | | 18 | | |
| 1100 | | 0.42 | 14.0 | | 0.29 | 19.0 |
| 1200 | 12 | | | 19 | | |
| 1300 | | 0.41 | 8.0 | | 0.27 | 20.0 |
| 1500 | | 0.71 | 24.0 | | 0.39 | 22.0 |
| Total Flow | 62.98 liters | | | 101.57 liters | | |
| 0900 | 6 | 0.30 | 15.0 | 14 | 0.40 | 24.0 |
| 1100 | | 0.30 | 14.0 | | 0.64 | 16.0 |
| 1300 | 6 | 0.84 | 16.0 | 19 | 0.56 | 22.0 |
| 1500 | | 0.60 | 22.0 | | 0.61 | 22.0 |
| Total flow | 65.14 | | | 107.16 liters | | |
| 0900 | 6 | | | | | |
| 1000 | | Back flush | | 9.5 | 0.76 | 3.1 |
| 1400 | | | | | | |
| 1530 | | 0.56 | 6.0 | | | |
| Total flow 68.22 liters | | | | | | |
| 0800 | | 0.78 | 9.0 | | | |
| 0900 | 7 | | | | | |
| 1100 | 6 | 1.00 | 3.0 | | | |
| 1300 | | 0.99 | 10.0 | | | |
| 1400 | 6 | | | | | |
| 1500 | | 0.95 | 6.0 | | | |
| Total flow 70.46 | | | | | | |
| 0800 | 4 | | | | | |
| 0900 | 4.5 | | | | | |
| 1300 | 4.0 | | | | | |
| Grand Total (Flow) | 70.46 liters | | | 107.16 liters 446 bed vol. | | |

We claim:

1. Method of removing iron compounds from a phenolic composition containing up to 10% water comprising passing the phenolic composition through a bed of resin containing active sites of the general formula $$\left[\begin{array}{c} R-N \diagup CH_2-R^1 \\ \phantom{R-N}\diagdown H \phantom{xx} CH_2R^2 \end{array}\right]^+$$

where R is an inert active site connector and $R^1$ and $R^2$ are independently selected from the group consisting of H and COOH.

2. Method of claim 1 wherein the phenolic composition is phenol.

3. Method of claim 1 followed by regeneration of the resin with water.

4. Method of claim 1 wherein the residence time of the phenolic composition in the bed is from about 1 minute to about 15 minutes.

5. Methd of maintaining low concentrations of iron in a phenol process stream which may occasionally contain more than 5% water comprising passing said phenol process stream successively through (1) a bed of resin containing weakly basic active sites of the general formula $$\left[\begin{array}{c} R-N \diagup CH_2-R^1 \\ \phantom{R-N}\diagdown H \phantom{xx} CH_2-R^2 \end{array}\right]^+$$

where R is an inert active site connector and $R^1$ and $R^2$ are independently selected from H and COOH, and (2) a bed of strongly acidic ion exchange resin.

6. Method of claim 5 including periodically backwashing the beds of resin.

7. Method of claim 5 wherein the residence time of the phenol process stream in the weakly basic resin is about 1 minute to about 15 minutes.

* * * * *

UNITED STATES PATENT AND TRADEMARK OFFICE
CERTIFICATE OF CORRECTION

PATENT NO. : 4,370,240

DATED : January 25, 1983

INVENTOR(S) : George L. Brownell, William R. Davie and Marvin C. Fields

It is certified that error appears in the above—identified patent and that said Letters Patent is hereby corrected as shown below:

Column 9, line 60, Table D, IRC 718 Resin, under "Time", change "0903"

to -- 0930 --.

Signed and Sealed this

Tenth Day of May 1983

[SEAL]

Attest:

GERALD J. MOSSINGHOFF

Attesting Officer

Commissioner of Patents and Trademarks